United States Patent [19]

Orbán et al.

[11] Patent Number: 5,206,016
[45] Date of Patent: Apr. 27, 1993

[54] CREAM CONTAINING ALUMINUM POTASSIUM SULFATE AND PROCESS FOR PREPARING SAME

[75] Inventors: Ernö Orbán; Péter Várnai, both of Budapest, Hungary

[73] Assignee: Florin Vegyipari Szövetkezet, Szeged, Hungary

[21] Appl. No.: 792,854

[22] Filed: Nov. 19, 1991

[30] Foreign Application Priority Data

Nov. 14, 1991 [HU] Hungary .............................. 3568/91

[51] Int. Cl.⁵ .............................................. A61K 9/107
[52] U.S. Cl. .................................... 424/401; 424/698; 514/938
[58] Field of Search ............... 424/698, 709, 682, 401; 514/938

[56] References Cited

U.S. PATENT DOCUMENTS

| | | | |
|---|---|---|---|
| 3,856,941 | 12/1974 | Turner | 424/682 |
| 4,120,948 | 10/1978 | Shelton | 424/401 |
| 4,191,750 | 3/1980 | Hodosh | 424/682 |
| 4,708,865 | 11/1987 | Turner | 424/63 |
| 5,091,194 | 2/1992 | Hankó | 424/698 |

Primary Examiner—Thurman K. Page
Assistant Examiner—Amy L. Hulina
Attorney, Agent, or Firm—Keil & Weinkauf

[57] ABSTRACT

The invention relates to a novel oil-in-water type cream containing aluminum potassium sulfate, which is useful for the treatment of varicosity. The composition of the invention contains 1 to 15% by weight of pharmaceutically acceptable lipid-type ointment base, 0 to 10% by weight of aluminum potassium sulfate dissolved in water, 10 to 80% by weight of propylene glycol and 0.1 to 5.0% by weight of cetyltrimethylammonium bromide and/or cetyltrimethylammonium chloride as emulsifying agent.

8 Claims, No Drawings

CREAM CONTAINING ALUMINUM POTASSIUM SULFATE AND PROCESS FOR PREPARING SAME

This invention relates to a novel, therapeutically effective composition, more particularly to an aluminum potassium sulfate-containing cream, which is useful for the treatment of varicosity. The invention furthermore relates to a process for preparing this novel cream.

Varicosity is a disease developing as a consequence of the alterations of superficial venous system and affects 15 to 17% of the adult population (people). The most important symptoms accompanying varicosity are: the extended veins with a winding pattern under the skin of thigh and leg, which are well-visible in orthostatic position. Secondary changes are: the thinning and brownish pigmentation of skin, an extended tumescence, fibrosis and distal exulceration of the leg.

Concerning the complications, the exulceration developing after the thinning of skin, which eventually extends to the varix, may be the source of a profuse bleeding. The acute or subacute forms of thrombophlebitis as well as thrombo-embolic complications are frequent. Fungal or bacterial dermatitis connected with vascular disturbances may also be mentioned.

Varicosity is treated in a surgical or nonsurgical way or by medication. The surgical treatment consists of interrupting and removing the varicose as well as incompetent, perforated veins. Concerning the prevention of a relapse, the most important element of the surgical intervention is the accurate finding and complete provision of the sapheno-femoral junction. Sclerotherapy by compression, inducing an obliteration and prolonged fibrosis in the collapsed veins, represents a transition between surgical and nonsurgical solutions.

A general treatment consisting of the simultaneous use of nonsurgical methods is useful mainly in the early varicosity, before the development and for prevention of secondary laesions. It can be used for aged persons and for those wanting to delay operation, as well as in the cases of a mild varicosity without complaints. This type of treatment includes e.g.: the wearing of flexible stockings and bandage on the proximal part of foot and on the leg; or shelving of the extremity, a method of lowering the venous pressure, is also a reasonable therapy.

A few solutions are only known for the treatment by medication of this disease. One of the best known of these is the topical use of aluminum potassium sulfate leading to a significant improvement of the inconvenient symptoms accompanying varicosity.

Aluminum potassium sulfate (1:1:2) [Alk(SO$_4$)2.12-H$_2$O], i.e. alum (USP XXII) is a substance of long therapeutical use. Due to its strong astringent and significant antiseptic effects, it is widely used in solid form as a styptic (haemostatic agent) and as a rinsing agent in solution [Martindale: The Extra Pharmacopoeia, 19. Ed. The Pharmaceutical Press, London (1989)].

When used topically, alum is employed in a solution of 0.5 to 5% concentration for various skin and mucous membrane lotions as well as for gargling, irrigation and the like.

Compositions containing aluminum potassium sulfate for the treatment of varicosity have been commercialized by the Florin company (Szeged, Hungary) under the trade names Varikopax B ® and Varikopax-super ®, respectively. These compositions contain alum in an amount over 10% incorporated in a known ointment base. Their use is complicated because alum is present in a form of a solid (powder) and not in a solution in the above compositions therefore, the active ingredient cannot act on the skin surface after applying the paste without an after-treatment. According to the instructions given for the use of the above compositions, the paste has to be diluted with water on the skin surface, which results in the formation of a solution ensuring the therapeutical effect.

This latter procedure is unusual in an ointment therapy, it is inconvenient to the patient and the treatment is made extremely complicated by this use.

An important drawback of the compositions mentioned above consists therein, that a part of the solid alum is only dissolved from the paste applied onto the skin surface therefore, the bioavailability of alum is extremely low.

On embrocation, the thinned skin may be injured and a bleeding may be induced by the alum particles precipitated from the paste.

The aim of the present invention is to develop a cream containing aluminum potassium sulfate, which is easy to wash off with water, which is free from the drawbacks of known solvings, contains aluminum potassium sulfate in a dissolved and not in a solid form, whereby the effect can directly be exerted without any after-treatment and, due to the softness of the cream, the treatment becomes simple and easy for the patient.

The main difficulty of preparing an emulsion containing alum solution is to find out an emulsifying agent ensuring the stability of the disperse system for a long time (i.e. for several years). It is known from literature that, due to their salting out effect, strong electrolytes such as alum, deprive the emulsifying agent from its hydrate layer, which induces the flocculation of the dispersed particles.

The process of salting-out is based thereon that the water/ion bonds existing in elecrolyte solutions are stronger than the original water/water bonds and the structure of water is broken by preventing the formation of hydrogen bonds between the ions and the next water molecules [Emulsions and Emulsion Technology, Part I., Ed. by K. J. Lissant, Marcel Dekker INC, New York (1974)].

The salting-out effect of electrolytes on neutral molecules such as various surface active agents is defined by the length of ionic radious of the salting-out component as well as by the concentration of the electrolyte.

In order to achieve a useful effect, the alum-containing cream used for the treatment of varicosity has to be prepared in a concentration significantly exceeding the electrolyte concentration of the known cosmetical or therapeutical creams. Consequently, the salting-out effect of alum has to be considered as more important than it is commonly usual in the preparation of creams.

During our investigations aimed to develop a stable cream containing alum groups of nonionic, anionic, cationic and amphoteric surface active agents have been examined as emulsifying agents. Thus, the following substances have been subjected to examination.

From the nonionic surface active agents: glyceryl monostearate, tetraglyceryl monooleate, sucrose mono-, di- or triacylate, PEG-8 laurate, PEG-400 monolaurate, polyoxyethylene (8) monolaurate, polysorbate 40, sorbimacrogol palmitate 300, polyoxyethylene (20) sorbitan monopalmitate, PEG-1000 cetyl ether, PEG-20 cetyl ether, polyoxyethylene (20) cetyl ether, polyoxyethylene (3) tridecyl ether, polypropylene glycol (18) butyl ether, polyoxypropylene (18) butyl ether and Poloxamer 401.

From the anionic surface active agents: sodium palmitate, calcium stearoyl-2-lactylate, sodium lauryl sulfate, dioctyl sodium sulfosuccinate, and diethanolammonium polyoxyethylene (10) oleyl ether phosphate.

From the cationic surface active agents: PEG-15 cocamine, cetyltrimethylammonium bromide and chloride (CTAB and CTAC, respectively).

From the amphoteric surface active agents: 1,2-diacyl-L-phosphatidyloholine and myristoamphoacetate.

On examining the stability of alum-containing emulsions prepared by using the above surface active agents, it has been stated that there exists an incompatibility between alum and the anionic surface active agents therefore, the surfactants of this group are unsuitable for the preparation of dispersions.

The results obtained by using nonionic surface active agents have shown that dispersions can be prepared by using emulsifying agents of this group, however, due to the salting-out effect of alum, a gradual separation of the phases occurred in these dispersions after a few weeks of storage.

The same phenomenon has been observed also in the case of amphoteric surface active agents investigated, as well as with PEG-15 cocamine belonging to the group of cationic surface active agents.

However, it has surprisingly been found during stability study carried out on CTAB and CTAC, respectively, that emulsions containing an alum solution prepared by using CTAB or CTAC maintained their original structure even after 2 years, i.e. no dehydratation of the surface active agent proceeded in the system thus obtained.

The above recognition is also surprising since several mentions have been made in the literature about the salting-out effect of electrolytes against various surface active agents, which is a phenomenon occurring between an electrolyte and neutral molecules; however, no reference can be found concerning the resistance to electrolytes of CTAB and CTAC described by us (described in the present patent application). [Emulsion Science, Ed. by P. Sherman, Academic Press, London and New York (1968)].

By the means of above surface active agents, by using some pharmaceutically acceptable additives an oil-in-water (o/w) type cream containing alum has been prepared. Neither physical nor chemical alterations have been observed after storage of the experimental preparations (compositions) at an isothermal temperature of 5° C. or 25° C., respectively, for 2 years.

The creams thus prepared are soft and easy to apply onto the skin surface.

When the experimental compositions prepared by using CTAB and CTAC, respectively, were subjected to intense clinical trials, it has been observed both on outpatients and inpatients that after the treatment their subjective complaints were moderated in the primary varicosity of the lower extremities in its extended, medium severe forms; the pain, burning and itching sensations were substantially weakened. The objective symptoms (signs of enviromental inflammation, liability to edema, exudative phenomena) showed an improvement in about 85%. Neither adverse side effect, nor complications were found in any of the cases. Due to its softness and cooling effect, the cream was readily accepted by the patients.

Based on the above results the invention relates to a novel, therapeutically useful oil-in-water (o/w) cream comprising the aqueous solution of aluminum potassium sulfate as aqueous phase. The oily phase contains pharmaceutically acceptable ointment bases such as: hydrocarbons, e.g. mineral oil or petrolatum; triglycerides, e.g. cocoa oil, palm oil, cocoa butter, avocado oil, castor oil, synthetic fatty acid esters of glycerin (e.g. Miglyol-810, -812, -818, -840, Dynamit Nobel AG Troisdorf Oberlal Germany); hydrogenated triglycerides, e.g. hydrogenated peanut oil; high molecular alcohols, e.g. lauryl alcohol, myristyl alcohol, cetyl alcohol, stearyl alcohol, cetylstearyl alcohol, octyldodecanol, oleyl alcohol; lanolin alcohol; waxes, e.g. beeswax, wool wax, spermaceti; fatty acids, e.g. stearic acid; ethoxylated triglycerides, e.g. ethoxylated castor oil; or a mixture thereof.

The cream of the invention contains 0.1 to 5.0% by weight of cetyltrimethylammonium bromide and/or cetyltrimethylammonium chloride as emulsifying agent.

The composition according to the invention contains the aqueous phase in an amount of 20 to 90% by weight, preferably 40 to 90% by weight calculated for the cream.

The aqueous phase contains 1 to 15% by weight, preferably 3 to 7% by weight of alum expressed as $AlK(SO_4)_2 \cdot 12H_2O$ and 0 to 10% by weight of propylene glycol.

The cream according to the invention can be prepared by dissolving at room temperature alum in water, forming the outer phase of the cream and dissolving cetyltrimethylammonium bromide and/or cetyltrimethylammonium chloride in the solution thus obtained, then mixing propylene glycol to the solution and heating the solution to 55 to 75° C.

Subsequently, the components of the oily phase are mixed and heated to 55 to 75° C. The warm, oily and aqueous phases are combined in an ointment mixer and homogenized by stirring.

After combining both phases, the stirring is continued until the temperature of the emulsion reaches 25 to 30° C. Thereafter the cream arising due to the cooling is filled up (supplemented) with water in order to adjust its final weight.

The preparation is subjected to a repeated homogenization and then filled into hermetically closing electrolyte-resistant tubes or crucibles.

Thus, according to the process of the invention a stable alum-containing cream possessing good bioavailability and advantageous physical characteristics can be prepared by using pharmaceutically acceptable additives commonly employed.

The invention is illustrated in detail by the aid of the following non-limiting examples.

EXAMPLE 1

| Composition of the cream | % by weight |
| --- | --- |
| (O) Cetylstearyl alcohol | 4.0 |
| Octyldodecanol | 5.0 |
| Lanolin alcohol | 4.0 |
| Ethoxylated castor oil | 2.0 |
| White petrolatum | 2.0 |
| (W) Alum [$AlK(SO_4)_2 \cdot 12H_2O$] | 6.5 |
| Cetyltrimethylammonium chloride | 2.5 |
| Purified water | 74.0 |

The cream is formulated from the above ingredients in the following way.

Cetylstearil alcohol, ethoxylated castor oil, lanolin alcohol, octyldodecanol and white petrolatum weighed and mixed in the ratio defined above are heated to 60° C. Alum and CTAC are dissolved in water at room temperature, then the solution is heated to 62° C. Both phases are combined in an ointment mixer and homogenized by stirring. While stirring the cream is cooled to about 30° C. and its weight is supplemented with purified water as described in the formulation. Subsequently, the cream is again homogenized by stirring and then filled into an electrolyte-resistant storage bottle.

EXAMPLE 2

| Composition of the cream | % by weight |
| --- | --- |
| (O) White petrolatum | 20.0 |
| Cetylstearyl alcohol | 11.0 |
| Mineral oil, low viscosity | 8.0 |
| (W) Alum [AlK(SO$_4$)$_2$.12H$_2$O] | 4.0 |
| Cetyltrimethylammonium bromide | 1.3 |
| Purified water | 55.7 |

The cream is formulated from the above ingredients in the following way.

White petrolatum, cetylstearyl alcohol and mineral oil weighed and mixed in the ratio defined above are heated to 70° C.

Alum and CTAB are dissolved in water at room temperature and the solution is heated to 72° C. Both phases are combined in an ointment mixer and homogenized by stirring. While stirring the cream is cooled to about 30° C. and its weight is supplemented with purified water as described in the formulation. Subsequently, the cream is homogenized by stirring and then filled into an electrolyte-resistant storage bottle.

EXAMPLE 3

| Composition of the cream | % by weight |
| --- | --- |
| (O) White Petrolatum | 16.0 |
| Mineral oil, low viscosity | 14.0 |
| Lanolin | 3.5 |
| Lanolin alcohol | 3.0 |
| Beeswax | 1.2 |
| (W) Alum [AlK(SO$_4$)$_2$.12H$_2$O] | 6.0 |
| Cetyltrimethylammonium bromide | 3.0 |
| Purified water | 53.3 |

The cream is formulated from the above ingredients in the following way.

White petrolatum, mineral oil, lanolin, lanolin alcohol and beeswax weighed and mixed in the ratio defined above are heated to 70° C. Alum and CTAB are dissolved in water at room temperature and the solution is heated to 72° C. Both phases are combined in an ointment mixer and homogenized by stirring.

While stirring the cream is cooled to about 25° C. and its weight is supplemented with demineralized water as described in the formulation. Subsequently, the cream is homogenized by stirring and then filled into electrolyteresistant storage bottles.

EXAMPLE 4

| Composition of the cream | % by weight |
| --- | --- |
| (O) Hydrogenated Peanut oil | 20.0 |
| Cetyl alcohol | 10.0 |
| (W) Alum [Alk(SO4)$_2$.12H$_2$O] | 5.0 |
| Cetyltrimethylammonium bromide | 2.0 |
| Cetyltrimethylammonium chloride | 2.0 |
| Propylene glycol | 8.0 |
| Purified water | 53.0 |

The cream is formulated from the above ingredients in the following way.

Hydrogenated peanut oil and cetyl alcohol weighed and mixed in the ratio defined above are heated to 55° C. Alum, CTAC and CTAB are dissolved in water at room temperature, propylene glycol is added in the amount defined above and the solution is heated to 57° C.

Both phases are combined in an ointment mixer and homogenized by stirring. While stirring, the cream is cooled to about 30° C. and its weight is supplemented with purified water as described in the formulation.

Subsequently, the cream is homogenized by stirring, then filled into electrolyte-resistant bottles.

We claim:

1. An oil-in-water (o/w) cream composition containing aluminum potassium sulfate for therapeutical use which comprises:
    10 to 80% by weight an oily phase of pharmaceutically acceptable lipid ointment bases, and
    20 to 90% by weight of an aqueous phase comprising 1 to 15% by weight of dissolved aluminum potassium sulphate, 0 to 10% by weight of propylene glycol, 0.1 to 5.0% by weight of cetyltrimethylammonium bromide, cetyltrimethylammonium chloride or mixtures thereof and water, calculated from the total weight of the cream composition.

2. The cream composition of claim 1, which comprises the aqueous phase in an amount of 40 to 90% by weight calculated for the total weight of the composition.

3. The cream composition of 1, which comprises 3 to 7% by weight of aluminum potassium sulfate dissolved in the aqueous phase.

4. A process for the preparation of an oil-in-water (o/w) cream containing aluminum potassium sulfate for therapeutical use which comprises:
    10 to 80% by weight an oily phase of pharmaceutically acceptable lipid ointment bases, and
    20 to 90% by weight of an aqueous phase comprising 1 to 15% by weight of dissolved aluminum potassium sulphate, 0 to 10% by weight of propylent glycol, 0.1 to 5.0% by weight of cetyltrimethylammonium bromide, cetyltrimethylammonium chloride or mixtures thereof and water, calculated from the total weight of the cream,
    which process comprises dissolving the aluminum potassium sulfate and the cetyltrimethylammonium bromide, cetyltrimethylammonium chloride or mixtures thereof in water, optionally containing propylene glycol, and mixing the solution thus obtained with the pharmaceutically acceptable lipid ointment base.

5. The process of claim 4, which comprises using the aqueous phase in an amount of 40 to 90% by weight calculated for the total weight of the composition.

6. The process of claim 4, which comprises dissolving aluminum potassium sulfate in the aqueous phase in an amount of 3 to 7% by weight.

7. A process as claimed in claim 4, which comprises using cetyltrimethylammonium bromide and/or cetyltrimethylammonium chloride in an amount of 0.1 to 5.0% by weight calculated for the total weight of the composition.

8. A process as claimed in claim 4, which comprises using propylene glycol in an amount of 0 to 10% by weight calculated for the total weight of the composition.

* * * * *

UNITED STATES PATENT AND TRADEMARK OFFICE
CERTIFICATE OF CORRECTION

PATENT NO. : 5,206,016

DATED : April 27, 1993

INVENTOR(S) : ORBAN et al.

It is certified that error appears in the above-identified patent and that said Letters Patent is hereby corrected as shown below:

Claim 4, column 6, line 44, "propylent" should read --propylene--.

Signed and Sealed this

Eleventh Day of January, 1994

Attest:

BRUCE LEHMAN

Attesting Officer

Commissioner of Patents and Trademarks